United States Patent [19]

Quirk et al.

[11] Patent Number: 5,456,918
[45] Date of Patent: Oct. 10, 1995

[54] RANITIDINE PHARMACEUTICAL COMPOSITIONS

[75] Inventors: Christopher W. Quirk, Middx; David A. Jackson, Maidenhead; James M. Cameron, Oxfordshire, all of England

[73] Assignee: Glaxo Group Limited, London, England

[21] Appl. No.: 181,319

[22] Filed: Jan. 13, 1994

Related U.S. Application Data

[63] Continuation of Ser. No. 869,175, Apr. 16, 1992, abandoned, which is a continuation of Ser. No. 409,088, Sep. 19, 1989, abandoned.

[30] Foreign Application Priority Data

Sep. 20, 1988 [GB] United Kingdom ............ 8822071
Mar. 15, 1989 [GB] United Kingdom ............ 8905995

[51] Int. Cl.$^6$ ............................................ A61K 9/48
[52] U.S. Cl. .................... 424/451; 424/456; 424/464; 424/465; 424/489
[58] Field of Search .................... 424/451, 602, 424/488, 489; 514/370, 772.1, 456, 464, 465, 489

[56] References Cited

U.S. PATENT DOCUMENTS

| | | | |
|---|---|---|---|
| 3,944,660 | 3/1976 | Gottfried et al. | 424/44 |
| 4,140,760 | 2/1979 | Withington | 424/81 |
| 4,316,888 | 2/1982 | Nelson | 424/602 |
| 4,572,832 | 2/1986 | Kigasawa et al. | 514/772.1 |
| 4,636,498 | 1/1987 | La Mattina | 514/222 |
| 4,705,683 | 11/1987 | Dettmar | 424/81 |
| 4,792,452 | 12/1988 | Howard et al. | 424/468 |
| 4,814,341 | 3/1989 | Reiter | 514/370 |
| 4,824,664 | 4/1989 | Tarral et al. | 424/43 |
| 4,834,965 | 5/1989 | Martan et al. | 424/488 |
| 4,869,902 | 9/1989 | Buehler et al. | 424/686 |
| 4,996,222 | 2/1991 | Carlin et al. | 514/400 |

FOREIGN PATENT DOCUMENTS

| | | |
|---|---|---|
| 0290229 | 11/1988 | European Pat. Off. |
| 1538123 | 1/1979 | United Kingdom. |
| 2093697 | 9/1982 | United Kingdom. |
| 2207865 | 2/1989 | United Kingdom. |

OTHER PUBLICATIONS

Finn et al., *Gastroenterology*, 94(5), pt. 11, A128, May 1988.
Russell et al., *Am. J. Gastroenterology*, 83(9), 1025, Oct. 1988.
Anon, "Antiulcer Combinations for Reflux", Mims, 19, Apr. 15, 1988.
Chandra et al., Br. J. Clin. Pract., 43, 3, Mar. 1989.
Swinyard; "Gastrointestinal Drugs"; Remingtons Pharmaceutical Sciences; Chapter 39; pp. 774–778.

*Primary Examiner*—Thurman K. Page
*Assistant Examiner*—William E. Benston, Jr.
*Attorney, Agent, or Firm*—Bacon & Thomas

[57] ABSTRACT

The invention provides a pharmaceutical composition for use in human or veterinary medicine which comprises ranitidine or a physiologically acceptable salt thereof, alginic acid or a physiologically acceptable salt thereof, and a carbonate or bicarbonate. The composition preferably comprises 1.25% to 10% w/w ranitidine hydrochloride, 5% to 35% w/w alginic acid, and 2% to 15% w/w sodium bicarbonate and is preferably in the form of a capsule or tablet. The compositions are suitable for the treatment of gastrointestinal disorders and particularly reflux oesophagitis.

25 Claims, No Drawings

RANITIDINE PHARMACEUTICAL COMPOSITIONS

This application is a continuation of application Ser. No. 07/869,175, filed Apr. 16, 1992, which in turn is a continuation of application Ser. No 07/409,088, filed Sep. 19, 1989, both now abandoned.

This invention relates to improvements in the treatment of gastrointestinal disorders. More particularly it relates to pharmaceutical compositions containing ranitidine and alginic acid or an alginate.

Ranitidine is the approved name for N-[2-[[5-[(dimethylamino) methyl]-2-furanylmethyl]thio]ethyl]-N'-methyl-2-nitro-1,1-ethenediamine which, together with its physiologically acceptable salts, is described and claimed in British Patent Specification No. 1565966. Ranitidine is a potent histamine $H_2$-antagonist which, in the Form of its hydrochloride salt, is widely used in the treatment of conditions where there is an advantage in lowering gastric acidity. Such conditions include duodenal and gastric ulceration, reflux oesophagitis and Zollinger-Ellison syndrome. Ranitidine may also be used prophylactically in surgical procedures, and in the treatment of allergic and inflammatory conditions where histamine is a known mediator.

Alginic acid and alginate salts have long been used in the treatment of gastrointestinal disorders. Co-administration of alginic acid or an alginate with the $H_2$-receptor antagonist ranitidine provides a useful and advantageous combination For the treatment of disorders of this type, and is particularly useful For the treatment of conditions such as reflux oesophagitis. In reflux oesophagitis there is regurgitation of the stomach contents into the oesophagus, which produces heartburn and other symptoms and may lead to damage of the oesophageal mucosa. Ingestion of alginic acid or an alginate results in the Formation of a raft on the top of the contents of the stomach, which serves as a physical barrier to regurgitation and, in the event that reflux does occur, will preferentially bathe the oesophageal mucosa, thereby protecting it from exposure to gastric contents. The role of the $H_2$-antagonist ranitidine is to reduce the volume and acidity of the gastric juice. This, combined with the action of the alginic acid or alginate, constitutes an effective means for the relief of symptoms and promotion of healing.

Formation of a satisfactory raft on top of the contents of the stomach may be facilitated by the presence of a carbonate or bicarbonate, which reacts with the acid present in the stomach, thereby serving as a source of carbon dioxide. The presence of carbon dioxide serves to regulate the density of the raft.

The present invention thus provides a pharmaceutical composition for use in human or veterinary medicine, more particularly human medicine, which comprises ranitidine or a physiologically acceptable salt thereof, alginic acid or a physiologically acceptable salt thereof, and a carbonate or bicarbonate.

The carbonate or bicarbonate may be for example an alkali metal or alkaline earth metal carbonate or bicarbonate such as magnesium carbonate, calcium carbonate, sodium bicarbonate or potassium bicarbonate, of which calcium carbonate and, more especially, sodium bicarbonate, are preferred. Such compounds are antacids, and other conventional antacids such as aluminium hydroxide and/or magnesium trisilicate may also be included in the composition.

It is preferred that ranitidine should be employed in the composition according to the invention in the form of physiologically acceptable salt. Suitable salts include salts of inorganic or organic acids such as the hydrochloride, hydrobromide, sulphate, acetate, maleate, fumerate and astorbate salts. Ranitidine in the form of a hydrochloride salt is particularly preferred.

Suitable physiologically acceptable salts of alginic acid for use in the composition according to the invention include salts with metals, such as alkali metal salts e.g. sodium alginate and alkaline earth metal salts e.g. magnesium alginate. Compositions containing a mixture of alginic acid end one or more alginate salts are also included within the scope of the invention.

The amount of ranitidine, preferably in the form of physiologically acceptable salt, employed in the composition according to the invention for administration to man (of approximately 70 kg body weight) is preferably within the range of 50 to 300 mg, more preferably 50 to 150 mg, per dosage unit, expressed as the weight of free base. The ranitidine content of the compositions (in the form of either free base or a physiologically acceptable salt) may be, for example, in the range of 1.25% to 10% on a weight-to-weight (w/w) basis.

The amount of alginic acid or alginate salt may conveniently be within the normal dosage range for the compound in question, more particularly within the range of 200 mg to 1 g per dosage unit. The alminic acid or alginate salt may constitute, for example, 5% to 35% (w/w) of the composition.

The amount of carbonate or bicarbonate which is present in the composition may conveniently be within the range of 50 to 250 mg per dosage unit. The carbonate or bicarbonate may constitute, For example, 2% to 15% (w/w) of the composition.

The ratio of alginic acid or alginate salt to carbonate or bicarbonate is preferably in the order of 3:1 to 4:1 on a w/w basis.

A preferred composition according to the invention comprises ranitidine hydrochloride, alginic acid and sodium bicarbonate. More particularly, these three ingredients may be present in amounts of 1.25% to 10.% (w/w), 5% to 35% (w/w) and 2% to 15% (w/w) respectively.

The composition according to the invention, in unit dosage form, may be administered, For example, 1 to 4 times per day, preferably once or twice.

The dosage will depend on the route of administration and the condition being treated, and it will also be appreciated that it may be necessary to make routine variations to the dosage depending on the age and weight of the patient as well as the severity of the condition to be treated.

Compositions according to the invention, which are primarily intended For oral administration, may be Formulated in conventional manner using one or more physiologically acceptable carriers or excipients.

For oral administration, the pharmaceutical compositions may take the Form of, For example, tablets including chewable or suckable tablets, or hard or soft gelatin capsules including chewable soft gelatin capsules. Such compositions may be prepared by conventional means with pharmaceutically acceptable excipients such as binding agents (e.g. pregelatinised maize starch, polyvinylpyrrolidone or bydroxypropyl methylcellulose); Fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, For example, solutions, syrups or suspensions, or they may be presented as a dry product (in the form of, for example, a sachet presentation) for constitution with water of other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid).

The preparations may also contain buffer salts, flavouring, colouring and/or sweetening agents as appropriate. Suitable flavouring agents include for example fruit flavours, peppermint or liquorice. The sweetening agents may be for example bulk sweeteners such as sugars (e.g. sucrose or fructose) and/or intense sweeteners (e.g. aspartame).

Compositions for oral use in the form of capsules or, more particularly, tablets are preferred.

The pharmaceutical compositions of the invention may be prepared according to conventional techniques well known in the pharmaceutical industry. Thus, for example, the ranitidine or ranitidine salt, the alginic acid or elginate salt, and the carbonate or bicarbonate may be admixed together, if desired, with suitable excipients. Tablets may be prepared, for example, by direct compression of such a mixture or by wet granulation. Capsules may be prepared by filling the blend along with suitable excipients into hard gelatin capsules, using a suitable filling machine. A paste form of the blend may be filled into hard or soft gelatin capsules, using flavoured shells and/or excipients to produce chewable capsules.

The compositions for use according to the invention may, if desired, be presented in a peck or dispenser device which may contain one or more unit dosage forms containing the active ingredients. The pack may for example comprise metal or plastic foil, such as a blister pack. The peck or dispenser device may be accompanied by instructions for administration.

The following examples illustrate pharmaceutical compositions according to the invention, containing ranitidine hydrochloride, alginic acid, and sodium bicarbonate or calcium carbonate as the active ingredients. Ranitidine in the form of another physiologically acceptable salt or as the free base and/or a physiologically acceptable salt of alginic acid (e.g. sodium alginate) and/or another carbonate or bicarbonate may be formulated in a similar manner.

EXAMPLE 1

| Direct Compression Tablets | mg/tablet |
|---|---|
| (i) Alginic acid BPC | 500.0 |
| Renitidine hydrochloride | 168.0* |
| Microcrystalline cellulose NF | 177.0 |
| Calcium carbonate Ph. Eur | 150.0 |
| Magnesium Stearate BP | 5.0 |
| Compression weight | 1000.0 mg |
| (ii) Alginic Acid BPC | 500.0 |
| Ranitidine hydrochloride | 84.0** |
| Calcium Carbonate Ph. Eur | 125.0 |
| Microcrystalline Cellulose USNF | 186.5 |
| Magnesiun Stearate Ph. Eur | 4.5 |
| Compression weight | 900.0 mg |

*Equivalent to 150.0 mg free base.
**Equivalent to 75.0 mg free base.

The ranitidine hydrochloride and alginic acid were blended with the other ingredients. The resultant mix was compressed into tablets using a suitable tablet press and suitable punches.

The tablets may be Film coated with suitable film forming materials, such as hydroxypropyl methylcellulose, using standard techniques.

Tablets of other strengths and/or combination of doses may be prepared by appropriate alterations in the amounts of the active ingredients and the excipients and using punches to suit.

EXAMPLE 2

| Capsules | mg/capsule |
|---|---|
| (i) Ranitidine hydrochloride | 84.0 |
| Alginic Acid BPC | 500.0 |
| Sodium Bicarbonate Ph. Eur | 165.25 |
| Magnesium Stearate Ph. Eur | 0.75 |
| Fill weight | 750.0 mg |
| (ii) Ranitidine hydrochloride | 84.0 |
| Alginic acid BPC | 500.0 |
| Calcium carbonate | 166.0 |
| Starch 1500* | 100.0 |
| Fill weight | 850.0 mg |

*A form of directly compressible starch supplied by Colorcon Ltd., Oprington, Kent.

The ranitidine hydrochloride and alginic acid were blended with the other ingredients. The mix was filled into size 00 hard gelatin capsules, using suitable machinery. Other doses may be prepared by altering the fill weight and if necessary changing the capsule size to suit.

EXAMPLE 3

| Chewable Tablets | |
|---|---|
| (i) Direct Compression | mg/tablet |
| Ranitidine hydrochloride | 84.00 |
| Alginic acid | 500.00 |
| Sodium bicarbonate | 170.00 |
| Aluminium hydroxide | 100.00 |
| Magnesium trisilicate | 25.00 |
| Sucrose | 1066.00 |
| Flavouring | 20.00 |
| Aspartame | 15.00 |
| Magnesium stearate | 20.00 |
| | 2000.00 |

The ranitidine hydrochloride, alginic acid and sodium bicarbonate were blended with the other ingredients. The resultant mix was compressed into tablets using a suitable tablet press and suitable punches.

| (ii) Wet Granulation | mg/tablet | |
|---|---|---|
| Alginic acid | 250.00 | |
| Aluminiun hydroxide | 100.00 | |
| Magnesium trisilicate | 25.00 | Granules A |
| Laevulose (Fructose) | 1016.00 | |
| Flavour | 20.00 | |
| Water (to wet mass) | qs | |
| Granules A | 1411.00 | |
| Ranitidine hydrochloride | 84.00 | |
| Alginic acid | 250.00 | |
| Dried maize starch | 50.00 | |
| Sodiun bicarbonate | 170.00 | |

| (ii) Wet Granulation | mg/tablet |
| --- | --- |
| Aspartame | 15.00 |
| Magnesium stearate | 20.00 |
| | 2000.00 |

The intragranular ingredients listed under 'Granules A' are blended together and granulated with water to give a wet mass which is dried to constant moisture level. These granules are then dry sieved, blended with the remaining extragranular ingredients, and compressed into tablets using a suitable tablet press and suitable punches.

Tablets of other strengths end/or combination of doses may be prepared by appropriate alterations in the amounts of the active ingredients and the excipients, end using punches to suit.

We claim:

1. A pharmaceutical composition for use in human or veterinary medicine consisting essentially of 1.25% to 10% w/w of ranitidine or a physiologically acceptable salt thereof, 5% to 35% w/w of an alginate component selected from the group consisting of alginic acid and physiologically acceptable salts of alginic acid, and 2% to 15% w/w of an alkali metal or alkaline earth metal carbonate or bicarbonate.

2. A pharmaceutical composition according to claim 1 which said carbonate or bicarbonate is an alkali metal bicarbonate.

3. A pharmaceutical composition according to claim 2 in which said alkali metal bicarbonate is selected from the group consisting of sodium bicarbonate and potassium bicarbonate.

4. A pharmaceutical composition according to claim 1 in which said carbonate or bicarbonate is selected from the group consisting of alkaline earth metal carbonates and bicarbonates and alkali metal carbonates.

5. A pharmaceutical composition according to claim 1 containing a further antacid in addition to said carbonate or bicarbonate.

6. A pharmaceutical composition according to claim 5 in which said further antacid is selected from the group consisting of aluminum hydroxide, magnesium trisilicate and mixtures thereof.

7. A pharmaceutical composition according to claim 1 containing ranitidine in the form of ranitidine hydrochloride.

8. A pharmaceutical composition according to claim 1 in which said alginate component is alginic acid.

9. A pharmaceutical composition according to claim 1 in unit dose form containing from 50 to 300 mg per dosage unit of ranitidine expressed as the weight of free base.

10. A pharmaceutical composition according to claim 1 in which said alginate component and said carbonate or bicarbonate are present in a weight ratio in the order of 3:1 to 4:1.

11. A pharmaceutical composition for use in human or veterinary medicine consisting essentially of 1.25% to 10% w/w ranitidine hydrochloride, 5% to 35% w/w alginic acid, and 2% to 15% w/w sodium bicarbonate.

12. A pharmaceutical composition according to claim 11 which also contains a further antacid selected from the group consisting of aluminum hydroxide, magnesium trisilicate and mixtures thereof.

13. A pharmaceutical composition according to claim 11 in unit dose form containing from 50 to 150 mg per dosage unit of ranitidine expressed as the weight of free base.

14. A pharmaceutical composition according to claim 1 adapted for oral administration in the form of capsules.

15. A pharmaceutical composition according to claim 1 adapted for oral administration in the form of tablets.

16. A method for the treatment of a gastrointestinal disorder in a human or animal subject which comprises administering to a human or animal subject suffering from a gastrointestinal disorder an effective amount to relieve said disorder of a pharmaceutical composition consisting essentially of ranitidine or a physiologically acceptable salt thereof, alginic acid or a physiologically acceptable salt thereof, and an alkali metal or alkaline earth metal carbonate or bicarbonate.

17. A method according to claim 16 in which said pharmaceutical composition also contains a further antacid selected from the group consisting of aluminum hydroxide, magnesium trisilicate and mixtures thereof.

18. A method according to claim 16 in which said pharmaceutical composition is in unit dose form containing from 50 to 150 mg per dosage unit of ranitidine expressed as the weight of free base.

19. A method according to claim 16 in which said composition consisting essentially of ranitidine hydrochloride, alginic acid, and sodium bicarbonate.

20. A method according to claim 16 in which said composition consisting essentially of 1.25% to 10% w/w ranitidine hydrochloride, 5% to 35% w/w alginic acid, and 2% to 15% w/w sodium bicarbonate.

21. A pharmaceutical composition according to claim 9 in unit dose form containing 75 mg per dosage unit of ranitidine expressed as the weight of free base.

22. A method according to claim 16 in which said gastrointestinal disorder is heartburn.

23. A method according to claim 16 in which said pharmaceutical composition is in unit dose form containing 75 mg per dosage unit of ranitidine expressed as the weight of free base.

24. A method according to claim 23 in which said gastrointestinal disorder is heartburn.

25. A method according to claim 20, wherein the gastrointestinal disorder is reflux oesophagitis and the composition, after administration, forms a raft on the top of the contents of the stomach which forms a physical barrier to regurgitation.

* * * * *